Figure 1:
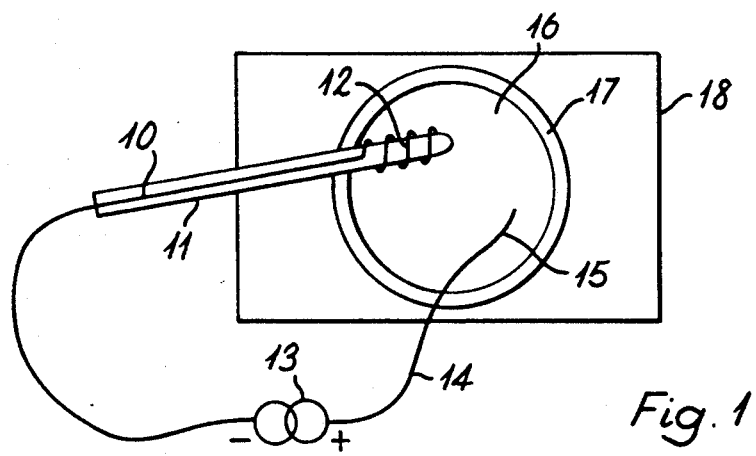

United States Patent [19]
Elliott et al.

[11] Patent Number: 5,154,165
[45] Date of Patent: Oct. 13, 1992

[54] MEDICAL DEVICES

[75] Inventors: Thomas S. J. Elliott, Sutton Coldfield; Phillip O. Byrne, Whickham, both of England

[73] Assignee: National Research Development Corporation, London, England

[21] Appl. No.: 797,162

[22] Filed: Nov. 26, 1991

Related U.S. Application Data

[63] Continuation of Ser. No. 554,090, Jul. 16, 1990, abandoned, which is a continuation of Ser. No. 363,478, Jun. 7, 1989, abandoned.

[30] Foreign Application Priority Data

Jun. 7, 1988 [GB] United Kingdom ............... 8813395

[51] Int. Cl.$^5$ .............................................. A61N 1/02
[52] U.S. Cl. .................................. 128/419 R; 604/20; 128/362
[58] Field of Search ............... 128/419 F, 419 R, 421, 128/787, 362; 600/11, 13, 14; 604/20, 21

[56] References Cited

U.S. PATENT DOCUMENTS

| | | | |
|---|---|---|---|
| 2,121,875 | 8/1933 | Kruse et al. | 128/362 |
| 2,276,623 | 3/1942 | Meiman | 128/787 |
| 2,456,909 | 12/1948 | Brasch | 128/421 |
| 2,482,507 | 9/1949 | Reutschler | 128/419 R |
| 2,655,922 | 10/1953 | Knappwost | 128/787 |
| 3,968,790 | 7/1976 | Fukuda et al. | 128/82.1 |
| 4,027,393 | 6/1977 | Ellis et al. | 604/20 |
| 4,314,554 | 2/1982 | Greatbatch | 604/20 |
| 4,411,648 | 10/1983 | Davis et al. | 604/21 |
| 4,528,265 | 7/1985 | Becker | 128/419 R |
| 4,569,673 | 2/1986 | Tesi | 604/20 |
| 4,572,194 | 2/1986 | Head | 128/419 R |
| 4,846,179 | 7/1989 | O'Connor | 128/419 R |
| 4,886,075 | 12/1989 | Jones | 128/787 |

FOREIGN PATENT DOCUMENTS

| | | | |
|---|---|---|---|
| 0134845 | 3/1985 | European Pat. Off. | 128/421 |
| 0140854 | 5/1985 | European Pat. Off. | 128/912 |
| 0140980 | 5/1985 | European Pat. Off. | 128/784 |
| 3240838A1 | 5/1984 | Fed. Rep. of Germany | 128/421 |
| WO86/07543 | 12/1986 | PCT Int'l Appl. | 128/419 F |
| WO89/02284 | 3/1989 | PCT Int'l Appl. | 128/787 |
| 230967 | 3/1926 | United Kingdom | 128/918 |
| 1286075 | 8/1972 | United Kingdom | 128/788 |
| 2195253A | 4/1988 | United Kingdom | 128/918 |

OTHER PUBLICATIONS

T. S. J. Elliott, "Intravascular Line Associated Infections—Prospects for Prevention", Medicom (UK) Ltd. 1987, pp. 13-16.

Primary Examiner—Francis Jaworski
Assistant Examiner—George Manuel
Attorney, Agent, or Firm—Nixon & Vanderhye

[57] ABSTRACT

A catheter or other invasive/implant device (40;52) intended for relatively long term use, of the order of a day or more, in a patient's body is provided with an electric field generator (48;53) to inhibit bacterial attachment and colonization on and adjacent the device/body interface. The generator can involve application to the device of electret material (53) or an electrode (48) in or for connection with an electrical circuit (47,50,51). The field is preferably unidirectionally negative and also continuous and constant, but pulsatile, alternating and other field forms are possible.

18 Claims, 2 Drawing Sheets

MEDICAL DEVICES

This is a continuation of application Ser. No. 07/554,909, filed Jul. 16, 1990, now abandoned, which is a Rule 62 continuation of U.S. Ser. No. 07/363,478 filed Jun. 7, 1989, now abandoned.

This invention concerns medical devices intended for relatively long term use, of the order of a day or more, in a location extending at least partially within a patient's body. Such devices include a variety of kinds, such as catheters, cannulae, shunts and orthopaedic endoprostheses, having a similar variety of primary functions and varyingly intended for deployment in a temporary or permanent role.

A fundamental problem associated with the use of such devices is that of infection. Infection in these circumstances is thought to involve the attachment of bacteria on the device surface which interfaces with the patient's body tissue and subsequent bacterial colonisation on and in the immediate vicinity of such surface. This situation is discussed, for example, in an article entitled "Intravascular line associated infections—prospects for prevention" by Dr. T. S. J. Elliott, presented at a symposium on "New Perspectives on Staphylococcus Infections" held September 1986, Lancashire, and thereafter published in 1987 in a booklet under the latter title by Medicom (UK) Limited. It will be seen from this article that various proposals for combative measures have yet to be established as satisfactory.

An object of the present invention is to reduce this infection problem by way of a measure involving, in general terms, provision of the device with means to generate an electric field over its interface surface, which field acts to inhibit bacterial attachment and colonisation on and adjacent that surface.

In one form of the invention the generating means comprises appropriately charged electret material applied over the device and so itself defines the interface surface, or such material applied in some other suitable manner.

In another form of the invention the generating means comprises a conductor for or in connection with an electrical circuit, the conductor being supported by the device and the circuit being operable to generate the appropriate field by way of the conductor. The conductor can be supported as a coating over the device and so itself define the interface surface, or it can be embedded as a wire or other configuration within the device suitably, in this event, to follow the outer surface shape of the device.

As so far developed the electric field is preferably negative to inhibit bacterial attachment by repulsion, the bacteria of concern commonly having negative surface charge. Such a field can also interfere with the bacterial charge, which charge plays a significant role in the attachment process.

Also, as so far developed the field is preferably continuously maintained in a substantially constant manner, but there is no reason to suppose that a pulsatile or otherwise varying negative field cannot be used to effect the desired action.

Indeed, it is not at present considered that the field should necessarily be unidirectionally negative. A field of alternating polarity can interfere with the ionic exchange process between the bacterial cell wall and surrounding medium and so act to inhibit colonisation. Moreover, an alternating field for this purpose need not necessarily be symmetrically cyclic, but can be asymmetrical.

Also, it is considered that the field of the invention can act against infection in other ways. For example, electroporation can be caused in cells subjected to the field and this could facilitate the action of drugs and/or natural immune response mechanisms on bacteria in the vicinity of the device. Moreover, to the extent that drugs, such as antibiotics, often exhibit a positive surface charge they can be beneficially attracted to and retained in the same vicinity.

Figure 2:
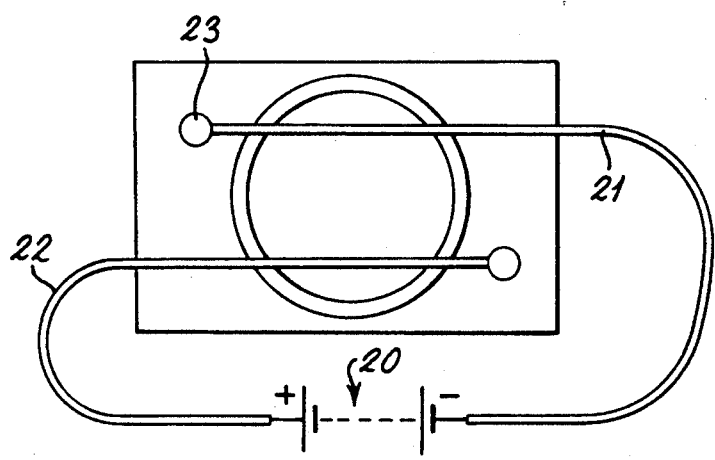
Figure 3:
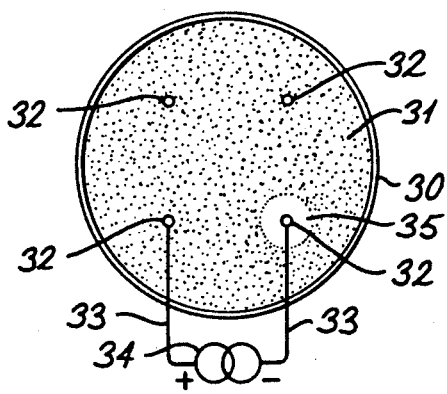
Figure 4:
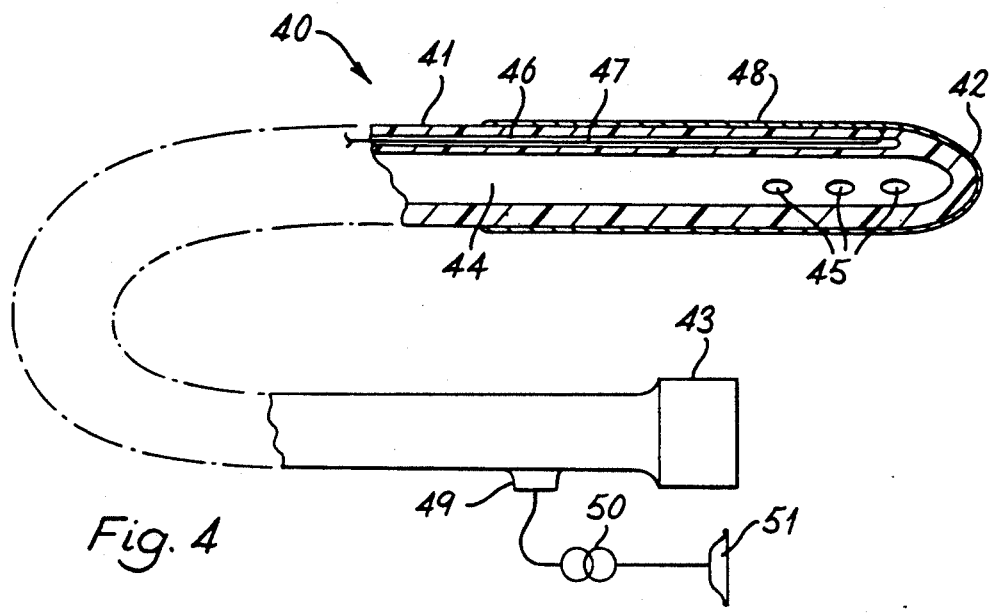
Figure 5:
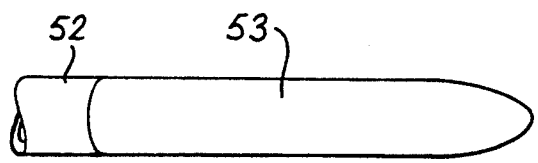
Figure 6:
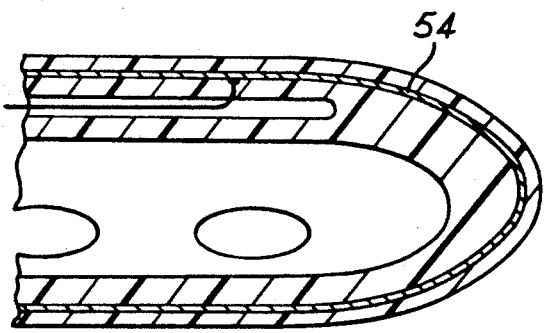

For further clarification of the invention, reference is made to the accompanying drawings in which:

FIGS. 1-3 diagrammatically illustrate respectively different experiments conducted during development of the invention, and FIGS. 4-6 similarly illustrate, by way of example, respectively different forms of device according to the invention.

In the experiment of FIG. 1 a stainless steel wire 10 was located along a plastics cannula 11 with a free end portion of the wire being wound around the tip portion of the cannula to form an electrode 12. The other end of the wire 10 was connected to the negative terminal of a constant current generator 13, a further stainless steel wire 14 being connected to the positive terminal of the generator and extending to an "indifferent" electrode 15 at its free end. The cannula tip plus its electrode 12 was placed, with the indifferent electrode 15, in mutually spaced manner in a turbid broth 16 of Staphylococcus epidermidis, at about $10^7$ cfu ml$^{-1}$, the broth being retained within the confines of an O-ring 17 mounted on a glass slide 18. The generator 13 was then operated to pass a small current of 1-10 μA between the electrodes for a period of 1-1.5 hours. After such operation clear areas appeared around the cannula and its electrode, that is to say there were insufficient bacteria in this area to make it turbid, and there were no bacteria visible on the cannula surface. At the same time the broth closely around the indifferent electrode appeared more turbid than that further spaced.

For comparative purposes the same arrangement was set up and left for 1.5 hours without generator operation and, in the result the broth remained evenly turbid.

In the experiment of FIG. 2 the same arrangement of slide, O-ring and broth was used as in FIG. 1 but with the other elements changed. In this case a D.C. source 20 had respective PVC insulated wires 21 and 22 connected to its terminals, the free end portions of these wires being located to pass through the broth in mutually spaced manner before securement to the slide with silicon sealant 23. Operation with the source applying a potential of about 100 V to the wires was considered effective to induce a small surface charge on the insulation surfaces of the wires. This charge was sufficient on the negative wire insulation to repel bacteria judged by the appearance of a clear zone in the broth around this wire.

In the experiment of FIG. 3 a petri dish 30 holding agar 31 was flooded with a broth of Staphylococcus epidermidis and allowed to dry such that about $10^6$ cfu bacteria were deposited, this being insufficient to give visible turbidity. Thereafter two pairs of hypodermic needles 32 were inserted in the agar in like mutually spaced manner to serve as electrodes. One such pair of electrodes was connected by wires 33 to respective terminals of a constant current source 34, while the other pair were left unconnected as control electrodes, and the dish incubated overnight at 37° C. with the source operating at about 10 μA. In the result the bacteria grew to form a confluent turbid lawn over the agar surface except for a clear zone 35 of about 3 mm diameter around the electrode connected to the source negative terminal, in which zone there was no bacterial growth.

The device of FIG. 4 is a catheter 40 comprising an elongate tubular body 41 of plastics material. The distal end portion or tip has a rounded closed end 42, while the proximal end portion terminates in a socket 43 of Luer or other form. The catheter is of double lumen form, having a larger lumen 44 communicating the socket 43 with apertures 45 in the wall of the tip for fluid transmission through the catheter, and a smaller lumen 46 closed at its ends. A wire 47 extends through the smaller lumen 46 and at its ends penetrates the catheter wall in sealed manner. The distal end portion for entry into a patient has an external electrode coating 48 of metal, carbon or other conductive material connected with the adjacent end of wire 47 and at the proximal end portion the end of the wire is connected with an electrical terminal 49.

In use the catheter will be connected by way of terminal 49 with the negative terminal of a constant current generator 50, suitably powered by a 1.5 V battery to generate an output of 1–10 μA, the generator having its positive terminal connected to a skin electrode 51 of conventional form, such as used in ECG monitoring and the like, for application to the patient.

The device of FIG. 5 comprises a simple single lumen catheter 52 having, over its distal end portion for entry in a patient, a coating 53 of persistent negatively-charged electret material. The charge on this material need only be such as to produce an electric field extending from the catheter up to a few tenths of 1 mm: the body, being an ionic conductor, will not allow a more extensive field to be established.

The device of FIG. 6 is similar to that of FIG. 4 except that in this case the distal electrode, denoted at 54, is embedded within the material of the catheter body to follow the outer surface shape of the body. This electrode is subjected to a potential of about 100 V by a battery-powered dc-to-dc converter having a current output limitation facility set no higher than 1 μA for patient safety in the event of breakdown of the catheter material insulation around the electrode during use.

We claim:

1. A method of reducing infection arising as a result of a device being at least partially placed within a patient's body, said method comprising the steps of:
   providing a field generating means comprising two electrodes and a separate power source connected between said electrodes for generating a persistent negative electric field around said device for repelling bacteria; and
   while said device is at least partially placed within said body, repelling said bacteria by generating said persistent negative electric field for the order of at least a day, whereby bacterial attachment and colonization in and adjacent the device/body interface is inhibited.

2. A method according to claim 1, wherein one of said electrodes forms at least part of the outer surface of said device to define said interface.

3. A method according to claim 1, wherein one of said electrodes is embedded in said device to follow at least part of the outer surface shape thereof.

4. A method according to claim 1, wherein said field is unidirectionally negative.

5. A method according to claim 4, wherein said field is continuously maintained in a subsequently constant manner.

6. A method according to claim 4, wherein said field is pulsatile.

7. A method according to claim 1, wherein one of said electrodes is intimately connected with said device and the other of said electrodes is connected with said device remotely by way of said power source, said method comprising:
   placing said one electrode within said body together with said device to generate said field, and
   placing said other electrode on the skin of said body.

8. A method according to claim 7, wherein said power source is a battery having negative and positive terminals and said one and other electrodes are respectively connected to said terminals.

9. A method of reducing infection arising as a result of the presence of a device being at least partially placed within a patient's body, said method comprising the steps of:
   providing a field generating means comprising an electret material for generating a persistent negative electric field around said device for repelling bacteria; and
   while said device is at least partially placed within said body, repelling said bacteria by generating said negative persistent electric field for the order of at least a day, whereby bacterial attachment and colonization in and adjacent the device the device/body interface is inhibited.

10. A method according to claim 9, wherein said electret material forms at least part of the outer surface of said device to define said interface.

11. A method of reducing infection arising as a result of the presence of a device being at least partially placed within a patient's body, said method comprising the steps of:
   providing a field generating means comprising an electret material for generating a persistent negative electric field around said device for repelling bacteria; and
   while said device is at least partially within said body, repelling said bacteria by generating said negative persistent electric field for the order of at least a day as a sole electrical measure for inhibiting bacterial attachment and colonization in and adjacent the device/body interface.

12. A method according to claim 11, wherein said electret material forms at least part of the outer surface of said device to define said interface.

13. A method of reducing infection arising as a result of the presence of a device being at least partially placed within a patient's body, said method comprising the steps of:
   providing a field generating means comprising two electrodes and a separate power source connected between said electrodes for generating a persistent negative electric field extending around said device for repelling bacteria; and
   while said device is at least partially placed within said body, repelling said bacteria by generating said negative persistent electric field for the order of at least a day as a sole electrical measure for inhibiting bacterial attachment and colonization in and adjacent the device/body interface.

14. A method according to claim 13, wherein one of said electrodes forms at least part of the outer surface of said device to define said interface.

15. A method according to claim 13, wherein one of said electrodes is embedded in said device to follow at least part of the outer surface shape thereof.

16. A method according to claim 13, wherein said field is unidirectionally negative.

17. A method according to claim 16, wherein said field is continuously maintained in a substantially constant manner.

18. A method according to claim 16, wherein said field is pulsatile.

* * * * *